US012590162B2

(12) United States Patent
Polymeropoulos et al.

(10) Patent No.: US 12,590,162 B2

(45) **Date of Patent: *Mar. 31, 2026**

(54) CANCER TREATMENT

(71) Applicant: Vanda Pharmaceuticals Inc., Washington, DC (US)

(72) Inventors: Mihael H. Polymeropoulos, Potomac, MD (US); Louis William Licamele, Potomac, MD (US); Christian Lavedan, Potomac, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/306,601

(22) Filed: Apr. 25, 2023

(65) Prior Publication Data

US 2023/0257471 A1 Aug. 17, 2023

Related U.S. Application Data

(63) Continuation of application No. 17/359,986, filed on Jun. 28, 2021, now Pat. No. 11,667,718, which is a continuation of application No. 16/357,249, filed on Mar. 18, 2019, now Pat. No. 11,078,289, which is a continuation of application No. 15/980,644, filed on May 15, 2018, now Pat. No. 10,265,282, which is a continuation of application No. 14/912,077, filed as application No. PCT/US2014/052209 on Aug. 22, 2014, now abandoned.

(60) Provisional application No. 61/869,039, filed on Aug. 22, 2013.

(51) Int. Cl.

| | |
|---|---|
| ***A61K 9/00*** | (2006.01) |
| ***A61K 9/08*** | (2006.01) |
| ***A61K 9/10*** | (2006.01) |
| ***A61K 9/107*** | (2006.01) |
| ***A61K 9/48*** | (2006.01) |
| ***A61K 31/165*** | (2006.01) |
| ***C07K 16/28*** | (2006.01) |
| *A61K 38/00* | (2006.01) |
| *A61K 39/00* | (2006.01) |

(52) U.S. Cl.

CPC ........ *C07K 16/2866* (2013.01); *A61K 9/0019* (2013.01); *A61K 9/0053* (2013.01); *A61K 9/0095* (2013.01); *A61K 9/08* (2013.01); *A61K 9/10* (2013.01); *A61K 9/107* (2013.01); *A61K 9/48* (2013.01); *A61K 31/165* (2013.01); *A61K 38/00* (2013.01); *A61K 2039/505* (2013.01); *C07K 2317/21* (2013.01); *C07K 2317/565* (2013.01); *C07K 2317/76* (2013.01)

(58) Field of Classification Search

CPC .......... A61P 35/00; A61P 35/02; A61P 43/00; A61K 9/0019; A61K 9/0095; A61K 9/48

See application file for complete search history.

(56) References Cited

U.S. PATENT DOCUMENTS

| | | | | |
|---|---|---|---|---|
| 4,218,478 | A | 8/1980 | Omura | A61K 31/165 514/619 |
| 4,690,918 | A | 9/1987 | Beppu | |
| 9,296,753 | B2 | 3/2016 | Smyth | A61P 9/00 |
| 9,670,549 | B2 * | 6/2017 | Mock | A61K 31/439 |
| 10,265,282 | B2 * | 4/2019 | Polymeropoulos | A61K 9/107 |
| 11,078,289 | B2 * | 8/2021 | Polymeropoulos | A61K 9/0095 |
| 11,667,718 | B2 * | 6/2023 | Polymeropoulos | A61K 31/165 424/133.1 |
| 11,737,993 | B2 | 8/2023 | Polymeropoulos | |
| 2002/0183388 | A1 | 12/2002 | Gudas et al. | |
| 2005/0260664 | A1 | 11/2005 | Shaughnessy et al. | |
| 2009/0123925 | A1 | 5/2009 | Collie-Duguid | |

FOREIGN PATENT DOCUMENTS

| | | | |
|---|---|---|---|
| EP | 0196415 | A2 | 10/1986 |
| EP | 3026006 | | 6/2016 |
| JP | 61176523 | A2 | 8/1986 |
| JP | 2007521259 | | 8/2007 |
| JP | 2010516628 | | 5/2010 |
| JP | 2020073508 | | 5/2020 |
| WO | 02060430 | A1 | 8/2002 |
| WO | 2007067516 | A2 | 6/2007 |
| WO | 2007139939 | A2 | 12/2007 |
| WO | 2010064016 | A2 | 6/2010 |
| WO | 2011134898 | A1 | 11/2011 |
| WO | 2013083098 | A2 | 6/2013 |
| WO | 2015027125 | A1 | 2/2015 |

OTHER PUBLICATIONS

Chinese Second Office Action and Search Report for Application No. 201480046624.5, dated Oct. 19, 2018.

Chen, New Ideas and New Targets in Pharmacological Research, 2012, pp. 85-86.

Liu et al., "Trichostatin A Affects Breast Cancer Cell Viability by Modulating Fhit and Survivin Expression," Biomedical Engineering and Biotechnology (ICBEB), 2012 International Conference on, IEEE. pp. 1133-1135 (2012).

Park et al., "Inhibitors of histone deacetylases induce tumor-selective cytotoxicity through modulating Aurora-A kinase," Journal of Molecular Medicine. 86(1):117-28 (2007).

Vigushin, "Trichostatin A is a histone deacetylase inhibitor with potent antitumor activity against breast cancer in vivo," Clinical Cancer Research. p. 971 (2001).

Wang et al., "Overexpression of aurora kinase A in mouse mammary epithelium induces genetic instability preceding mammary tumor formation," Oncogene. 25(54):7148-58 (2006).

(Continued)

*Primary Examiner* — Pancham Bakshi

(74) *Attorney, Agent, or Firm* — Hoffman Warnick LLC

(57) ABSTRACT

The invention relates generally to the treatment of cancer. One embodiment of the invention provides a method of treating cancer in an individual, the method comprising: administering to the individual an effective amount of trichostatin A (TSA).

5 Claims, No Drawings

(56) References Cited

OTHER PUBLICATIONS

International Search Report and Written Opinion for PCT/US2014/052209, mailed Mar. 30, 2015, 18 pages.
Xu et al., J Am Soc Nephrol 21: 2041-2046. (Year: 2010).
Nadler et al., Clin Cancer Res 2008;4455 14(14) Jul. 15, 2008 (Year: 2008).
Reagan-Shaw et al., "Does translation from animal to human studies revisited," The FASEB Journal, Life Sciences Forum, vol. 22, pp. 659-661, Year 2007.
Zhang et al., (Cancer Biol & Therapy (2008) vol. 7, No. 9, pp. 1388-1397) (Year: 2008).
Ling et al., "Mechanisms of Proteasome Inhibitor PS-341-induced G2-M-Phase Arrest and Apoptosis in Human Non-Small Cell Lung Cancer Cell Lines," Clinical Cancer Research 9: 1145-1154 (2003).
Zhang et al., "Aurora A, Aurora B and survivin are novel targets of transcriptional regulation by histone deacetylase inhibitors in non-small cell lung cancer," retrieved from: (Online) Journal homepage: http://www.tandfonline.com/loi/kcbt20 on Dec. 15, 2016, 11 pages.
Notice of Reasons for Rejection for Japanese Application No. P2021-42699, dated Dec. 17, 2024, 9 pages.
Heller et al., "Genome-Wide Transciptional Response to 5-Aza-2'-Deoxycytidine and Trichostatin A in Multiple Myeloma Cells," Cancer Research. 68(1):44-54 (2008).
Moreaux et al., "Gene expression-based prediction of myeloma cell sensitivity to histone deacetylase inhibitors," British Journal of Cancer. 109(3):676-85 (2013).
International Search Report and Written Opinion for PCT/US2014/052216, mailed Nov. 3, 2014, 10 pages.
Office Action and English Translation thereof for Eurasian Patent Application No. 201690446/28 dated Nov. 28, 2016, 4 pages.
Office Action for U.S. Appl. No. 14/912,078 dated Nov. 14, 2017, 23 pages.
Ahn et al., "The histone deacetylase inhibitor, Trichostatin A, induces G2/M phase arrest and apoptosis in YD-10B oral squamous carcinoma cells," Oncology Reports, 2012, vol. 27, pp. 455-460.
Gorgun et al., "A novel Aurora-A kinase inhibitor MLN8237 induces cytotoxicity and cell-cycle arrest in multiple myeloma," BLOOD, Jun. 24, 2010, vol. 115, No. 25, pp. 5202-5213.
Nair et al., "Paradoxical effects of trichostatin A: inhibition of NF-Y-associated histone acetyltransferase activity, phosphorylation of hGCN5 and downregulation of cyclin A and B1 mRNA," Cancer Letters, 2001, vol. 166, pp. 55-64.
Nara et al., "Bortezomib Reduces the Tumorigenicity of Multiple Myeloma via Downregulation of Upregulated Targets in Clonogenic Side Population Cells," Plos One, Mar. 2013, vol. 8, No. 3, pp. 1-13.
Shaughnessy Jr. et al., "A validated gene expression model of high-risk multiple myeloma is defined by deregulated expressions of genes mapping to chromosome 1," BLOOD, Mar. 15, 2007, vol. 109, No. 6, pp. 2276-2284.
Hsu (Biochimica et Biophysica Acta vol. 1820 pp. 104-115 Published 2012) (Year: 2012).
Hong Chang et al., "Multiple myeloma patients with CKS1B gene amplification have a shorter progression-free survival pos", British Journal of Haematology, (20060817), vol. 135, ISSN 0004098599, pp. 486-491.
Shaughnessy J, "Amplification and overexpression of CKS1B at chromosome band 1q21 is associated with reduced levels of p27<Kip1> and an aggressive clinical course in multiple myeloma", Hematology, Harwood Academic Publishers, Luxemburg, LX, (Sep. 1, 2005), vol. 10, No. Suppl. 1, doi:10.1080/10245330512331390140, ISSN 1024-5332, pp. 117-126, XP009128866.

* cited by examiner

CANCER TREATMENT

CROSS-REFERENCE TO RELATED APPLICATIONS

This application is a continuation application of U.S. patent application Ser. No. 17/359,986, filed 28 Jun. 2021, which is a continuation of then U.S. patent application Ser. No. 16/357,249, filed 18 Mar. 2019, now U.S. Pat. No. 11,078,289, which is a continuation of then U.S. patent application Ser. No. 15/980,644, filed 15 May 2018, now U.S. Pat. No. 10,265,282, which is a continuation application of then U.S. patent application Ser. No. 14/912,077, filed 12 Feb. 2016, which is the US National Phase Application of PCT/US14/52209, filed 22 Aug. 2014, which claims priority to U.S. Provisional Patent Application Ser. No. 61/869,039, filed 22 Aug. 2013, each of which is hereby incorporated herein.

BACKGROUND

Histone deacetylase (HDAC) inhibitors have been investigated for their use in cancer therapies due to their ability to inhibit tumor cell growth with comparatively little toxicity. Known HDAC inhibitors include, for example, rocilinostat (ACY-1215), Zolinza (vorinostat), abexinostat hydrochloride (PCI-24781), suberoylanilide hydroxamic acid (SAHA), valporic acid (VPA), Pracinostat (SB939), PCI-24781 (CRA-024781), JNJ-26481585, Mocetinostat (MGCD0103, MG0103), Droxinostat, MC1568, Givinostat (ITF2357), Tubastatin A HCl, PCI-34051, Tacedinaline (CI994), and Panobiostat (LBH589, NVP-LBH589).

Aurora Kinase A (AURKA) is one member of a serine and threonine kinase family known to be important in maintaining normal mitotic chromosomal segregation. Its protein localizes in the centrosomes of interphase cells and in the spindle of mitotic cells. AURKA overexpression has been linked with carcinogenesis in humans and has been detected in tumors of the breast, gastric tissues, colorectal tissue, bladder, pancreas, ovaries, prostate, and lung. It is possible, however, for any cancer to overexpress AURKA, which may be determined, for example, by testing a tumor for AURKA overexpression. Inhibition of AURKA expression has been shown to reduce cell invasion in vivo. As such, AURKA, too, is a cancer treatment target, typically through small molecule inhibition. Known AURKA inhibitors include, for example, VE465, tozasertib (VX-680), MK-0457, MK-5108, Alisertib (MLN8237).

Due to the efficacy of HDAC inhibitors and AURKA inhibitors in blocking cancer progression on their own, studies have evaluated the effect of their combined administration in non-human cancer models. For example, Li et al. found that co-treatment with VPA and VE465 induced more apoptosis than either compound did alone. Similarly, Okabe et al. found a synergistic inhibitory effect on the proliferation of cancer cells through the administration of either vorinostat or pracinostat in combination with tozasertib. The studies leading to the discovery of the present invention were undertaken since even though the dual HDAC and AURKA blocking effect was desirable in the treatment of cancer, no single entity is generally known to have this dual effect.

SUMMARY

One embodiment of the invention provides a method of treating cancer in an individual, the method comprising: administering to the individual an effective amount of trichostatin A (TSA).

Another embodiment of the invention provides a pharmaceutical composition comprising: trichostatin A (TSA) as a sole or primary aurora kinase A (AURKA) inhibitor; and a pharmaceutically-acceptable excipient or carrier.

In another embodiment, the invention provides a method of treating a cancer in an individual, the method comprising: determining, from a tumor sample obtained from the individual's body, a level of aurora kinase A (AURKA) expression; and in the case that the level of AURKA expression is indicative of overexpression, administering to the individual an effective amount of trichostatin A (TSA).

In still other embodiments of the invention, treatment with TSA is combined with one or more other cancer treatments. Such other treatments may include, for example, small molecule AURKA inhibition. Such a combined treatment may, in some cases, decrease the AURKA level to near zero.

DETAILED DESCRIPTION

Trichostatin A (TSA or 7-[4-(dimethylamino)phenyl]-N-hydroxy-4,6-dimethyl-7-oxohepta-2,4-dienamide), is an antifungal antibiotic and a known class I and II HDAC inhibitor. The structure of TSA is shown in Formula I below.

Formula I

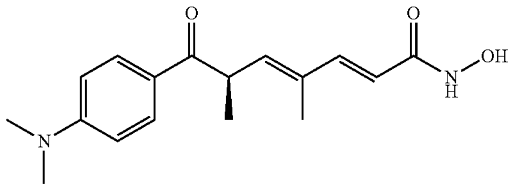

Applicants have surprisingly found that TSA, although previously known as an HDAC inhibitor, is also capable of inhibiting AURKA expression. As such, TSA may be used as the primary or sole AURKA inhibitor in the treatment of cancers. Cancers that may be treated according to embodiments of the invention include, for example, breast cancer, gastric cancer, colon cancer, rectal cancer, bladder cancer, pancreatic cancer, ovarian cancer, prostate cancer, lung cancer, hematological cancer, skin cancer, and malignancies.

A human retinal pigment epithelial cell line was treated with trichostatin or vehicle for 24 hours and gene expression for 22,238 probe sets covering 12,490 genes was generated using an Affymetrix instrument. The effect of trichostatin A on AURKA expression is shown below in Table 1, and indicates a clear more than ten-fold downregulation of AURKA expression.

TABLE 1

| InstanceID | Probe | Rank | Fold expression change | GeneName | Gene |
|---|---|---|---|---|---|
| 10005532 | 208079_s_at | 22253 | −20.0837023 | aurora kinase A | AURKA |
| 10005533 | 208079_s_at | 22245 | −18.95510102 | aurora kinase A | AURKA |

TABLE 1-continued

| InstanceID | Probe | Rank | Fold expression change | GeneName | Gene |
|---|---|---|---|---|---|
| 10005533 | 204092_s_at | 22238 | −17.32256882 | aurora kinase A | AURKA |
| 10005532 | 204092_s_at | 22227 | −15.79825298 | aurora kinase A | AURKA |
| 10005542 | 204092_s_at | 22222 | −14.33801143 | aurora kinase A | AURKA |
| 10005542 | 208079_s_at | 22221 | −14.19814583 | aurora kinase A | AURKA |

These results support the use of TSA in the treatment of cancer. For example, an individual may be treated for cancer by administering to the individual an effective amount of TSA, wherein the effective amount is an amount sufficient to inhibit expression of AURKA in the individual. Such an amount may also be sufficient to inhibit HDAC activity in the individual. In some embodiments of the invention, the effective amount is between about 0.1 mg/kg/day and about 10 mg/kg/day, e.g., between about 0.5 mg/kg/day and about 5 mg/kg/day.

In some embodiments, treating the individual may further comprise determining, from a tumor sample obtained from the individual's body, a level of AURKA expression. Such determining may include any known or later-developed method or technique, including, for example, quantitative antigen-antibody interactions, the use of labeled nucleotide probes, etc.

TSA may be administered to the individual to be treated in the form of a pharmaceutical composition. Pharmaceutical compositions to be used according to various embodiments of the invention comprise a therapeutically effective amount of TSA or an active metabolite of TSA, or a pharmaceutically acceptable salt or other form (e.g., a solvate) thereof, together with one or more pharmaceutically acceptable excipients or carriers. The phrase "pharmaceutical composition" refers to a composition suitable for administration in medical use. It should be appreciated that the determinations of proper dosage forms, dosage amounts, and routes of administration for a particular patient are within the level of ordinary skill in the pharmaceutical and medical arts.

Administration may be oral but other routes of administration may also be employed, e.g., parenteral, nasal, buccal, transdermal, sublingual, intramuscular, intravenous, rectal, vaginal, etc. Solid dosage forms for oral administration include capsules, tablets, pills, powders, and granules. In such solid dosage forms, the compound is admixed with at least one inert pharmaceutically-acceptable excipient such as (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid dosage forms such as tablets, drages, capsules, pills, and granules also can be prepared with coatings and shells, such as enteric coatings and others well known in the art. The solid dosage form also may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients. Such solid dosage forms may generally contain from 1% to 95% (w/w) of the active compound. In certain embodiments, the active compound ranges from 5% to 70% (w/w).

Solid compositions for oral administration can be formulated in a unit dosage form, each dosage containing from about 1 mg to about 500 mg of active ingredient. The term "unit dosage form" refers to physically discrete units suitable as unitary dosages for human subjects and other mammals, each unit containing a predetermined quantity of active ingredient calculated to produce the desired effect over the course of a treatment period, in association with the required pharmaceutical carrier. TSA can be formulated, e.g., in a unit dosage form that is a capsule having 1-500 mg of active in addition to excipients.

Liquid dosage forms for oral administration include pharmaceutically-acceptable emulsions, solutions, suspensions, syrups, and elixirs. In addition to the compound or composition, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances. Besides such inert diluents, the composition can also include adjuvants, such as wetting agents, emulsifying and suspending agents, sweetening, flavoring, and perfuming agents.

In some embodiments of the invention, TSA is provided in a liquid form and administered to an individual intravenously.

While this invention has been described in conjunction with the specific embodiments outlined above, it is evident that many alternatives, modifications and variations will be apparent to those skilled in the art or are otherwise intended to be embraced. Accordingly, the embodiments of the invention as set forth above are intended to be illustrative, not limiting. Various changes may be made without departing from the spirit and scope of the invention as defined in the following claims. All patents, patent application, scientific articles and other published documents cited herein are hereby incorporated in their entirety for the substance of their disclosures.

What is claimed is:

1. A method of treating a patient suffering from breast cancer, the method comprising:

determining, from a tumor sample of the patient, that the patient has increased aurora kinase A (AURKA) expression; and administering to the patient a dose of trichostatin A (TSA) of between about 0.1 mg/kg/day and about 10 mg/kg/day.

2. The method of claim 1, wherein the dose of TSA is between about 0.5 mg/kg/day and about 5 mg/kg/day.

3. The method of claim 1, wherein administering includes orally administering the dose of TSA.

4. The method of claim 1, wherein administering includes intravenously administering the dose of TSA.

5. The method of claim 1, wherein the dose of TSA is sufficient to inhibit histond deacetylase (HDAC) activity in the patient.

* * * * *